United States Patent
Wilder et al.

(10) Patent No.: US 10,065,005 B2
(45) Date of Patent: Sep. 4, 2018

(54) VAPORIZING DEVICES AND RELATED METHODS FOR CONTROLLING AN AMOUNT OF SUBSTANCE BEING VAPORIZED FOR CONSUMPTION BY A USER

(71) Applicant: S.E. Research and Design LLC, Raleigh, NC (US)

(72) Inventors: Robin Wilder, Golden, CO (US); Elizabeth Brooke Green, Golden, CO (US)

(73) Assignee: S.E. Research and Design LLC, Raleigh, NC (US)

( * ) Notice: Subject to any disclaimer, the term of this patent is extended or adjusted under 35 U.S.C. 154(b) by 0 days.

(21) Appl. No.: 15/699,001

(22) Filed: Sep. 8, 2017

(65) Prior Publication Data

US 2018/0177958 A1 Jun. 28, 2018

Related U.S. Application Data

(60) Provisional application No. 62/438,752, filed on Dec. 23, 2016.

(51) Int. Cl.
*A61M 15/00* (2006.01)
*A24F 47/00* (2006.01)

(52) U.S. Cl.
CPC .... *A61M 15/0066* (2014.02); *A61M 15/0021* (2014.02); *A24F 47/008* (2013.01)

(58) Field of Classification Search
CPC ...... A24F 47/00–47/008; A61M 11/00; A61M 11/041; A61M 11/042; A61M 11/08;
(Continued)

(56) References Cited

U.S. PATENT DOCUMENTS 6,461,322 B1   10/2002   Ritsche
9,861,136 B2 *  1/2018   Li .................... B65D 85/70
(Continued)

FOREIGN PATENT DOCUMENTS

FR       2293221 A1 *  7/1976  ............ A61M 15/00
WO    2006082571 A1    8/2006
(Continued)

OTHER PUBLICATIONS

Canadian Office Action for Application No. 2,979,458 dated Feb. 19, 2018.
(Continued)

*Primary Examiner* — Jackie Tan-Uyen T Ho
*Assistant Examiner* — Joseph D Boecker
(74) *Attorney, Agent, or Firm* — Olive Law Group, PLLC

(57) ABSTRACT

Vaporizing devices and related methods for controlling an amount of substance being vaporized for consumption by a user are disclosed herein. According to an aspect, a vaporizing device includes a casing configured to hold a substance for vaporizing. The vaporizing device also includes a plunger comprising a heating element inserted within the casing. The vaporizing device also includes a mechanism configured to advance the substance within the casing. Further, the vaporizing device includes a mouthpiece comprising an atomized configured to vaporize the material using the heating element.

10 Claims, 13 Drawing Sheets

(58) Field of Classification Search
CPC .............. A61M 15/00; A61M 15/0001; A61M 15/0021; A61M 15/0065; A61M 15/0066; A61M 15/06; A61M 2205/3653
See application file for complete search history.

(56) References Cited

U.S. PATENT DOCUMENTS

| | | | | |
|---|---|---|---|---|
| 9,861,141 | B1* | 1/2018 | Liu | A24F 47/008 |
| 2004/0050383 | A1* | 3/2004 | Cox | A61M 15/0003 |
| | | | | 128/200.14 |
| 2009/0133691 | A1* | 5/2009 | Yamada | A61M 11/041 |
| | | | | 128/200.16 |
| 2013/0228191 | A1* | 9/2013 | Newton | A24F 47/008 |
| | | | | 131/329 |
| 2013/0255675 | A1* | 10/2013 | Liu | A61M 11/041 |
| | | | | 128/202.21 |
| 2013/0319438 | A1* | 12/2013 | Liu | A24F 47/008 |
| | | | | 131/329 |
| 2014/0069424 | A1 | 3/2014 | Poston et al. | |
| 2015/0117842 | A1 | 4/2015 | Brammer et al. | |
| 2016/0219934 | A1* | 8/2016 | Li | A24F 47/008 |
| 2016/0360790 | A1* | 12/2016 | Calfee | A24F 47/008 |
| 2018/0027874 | A1* | 2/2018 | Zhu | A24F 47/008 |

FOREIGN PATENT DOCUMENTS

| | | |
|---|---|---|
| WO | 2013060827 A1 | 5/2013 |
| WO | 2016050244 A1 | 4/2016 |
| WO | 2016127293 A1 | 8/2016 |
| WO | 2016128562 A1 | 8/2016 |

OTHER PUBLICATIONS

Notice of Allowance issued in counterpart Canadian Application No. 2,979,458 dated May 28, 2018. (thirty-seven (37) pages).
International Search Report and Written Opinion issued in PCT application PCT/US2017/067508 dated May 17, 2018 (six (6) pages).

* cited by examiner

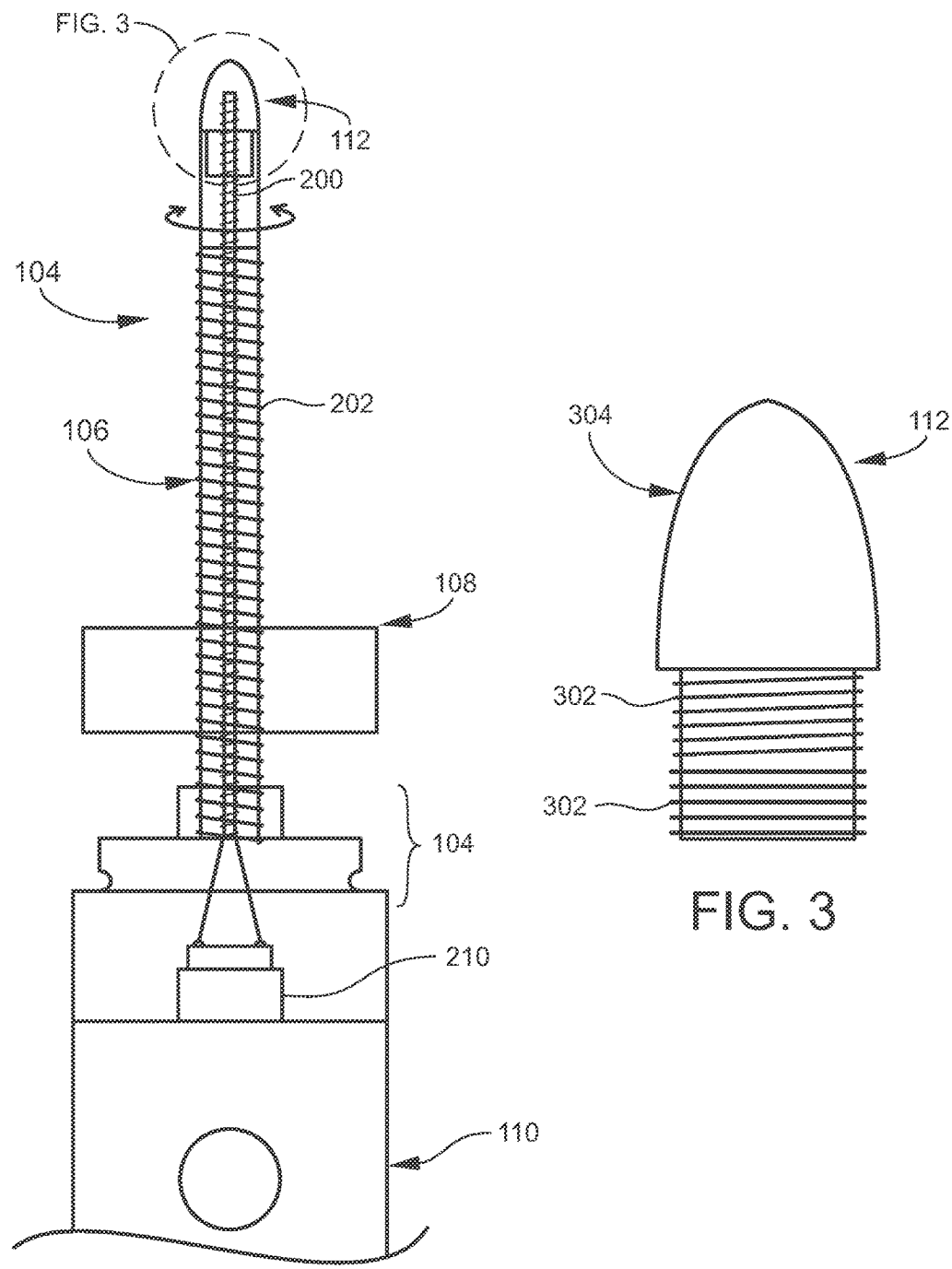

VAPORIZING DEVICES AND RELATED METHODS FOR CONTROLLING AN AMOUNT OF SUBSTANCE BEING VAPORIZED FOR CONSUMPTION BY A USER

CROSS REFERENCE TO RELATED APPLICATION

This application claims priority to U.S. Provisional Patent Application 62/438,752, filed Dec. 23, 2016, and titled VAPORIZING DEVICES AND RELATED METHODS, the entire content of which is incorporated herein by reference in its entirety.

TECHNICAL FIELD

The presently disclosed subject matter relates to vaporizing devices. More particularly, the presently disclosed subject matter relates to vaporizing devices for controlling an amount of substance being vaporized for consumption by a user.

BACKGROUND

A popular alternative to smoking tobacco based products, such as cigarettes, is inhaling vapors from a pen-sized vaporizing device, also known as electronic cigarettes. Some of these devices vaporize a substance, such as a liquid or oil, using a metal heating element that is in constant contact with the substance. Unfortunately, in these devices the substance of which a user is consuming may also be in constant contact with welds, glues, or by-products of vaporization. This increases the chance the user may consume potentially toxic vapors in addition to the vaporized substance. Thus, there is a need for a vaporizing device that can safely vaporize a substance without exposing user to toxic vapors.

Additionally, many known vaporizing devices fail to inform a user of an amount of substance either consumed or left for consumption in the vaporizing device. In some instances, a user may consume too much of the substance too quickly. In other instances, if too much of a substance is placed within the vaporizing device, the heating element may not vaporize the substance quickly enough. In such cases, the vaporized substance may take on a bitter taste to the user and waste the substance as it may no longer be desirable for consumption by the user. Therefore, in view of these difficulties, there is a need for improved vaporizing devices and techniques.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are vaporizing devices configured to control an amount of substance being vaporized for consumption by a user. According to an aspect, a vaporizing device includes a casing configured to hold a substance for vaporizing. The vaporizing device also includes a plunger comprising a heating element inserted within the casing. The vaporizing device also includes a mechanism configured to advance the substance within the casing. Further, the vaporizing device includes a mouthpiece comprising an atomized configured to vaporize the material using the heating element.

According to another aspect, a vaporizing device comprises a chamber configured to hold a substance for vaporizing. The vaporizing device also includes a heating chamber configured to couple to the chamber and vaporize the substance. The vaporizing device also includes a casing configured to receive the chamber and the heating element. The vaporizing device also includes a mechanism coupled to the casing and configured to advance the material within the chamber. Further, the vaporizing device includes a mouthpiece configured to receive the vaporized material from the mechanism.

BRIEF DESCRIPTION OF THE DRAWINGS

The foregoing summary, as well as the following detailed description of various embodiments, is better understood when read in conjunction with the drawings provided herein. For the purposes of illustration, there is shown in the drawings exemplary embodiments; however, the presently disclosed subject matter is not limited to the specific methods and instrumentalities disclosed.

FIG. 2 is a cross-sectional, side view of an example plunger including a heating element of a vaporizing device in accordance with embodiments of the present disclosure;

FIG. 3 is a side view of an example ceramic tip configured to receive a heating element of the plunger in accordance with embodiments of the present disclosure;

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Articles "a" and "an" are used herein to refer to one or to more than one (i.e. at least one) of the grammatical object of the article. By way of example, "an element" means at least one element and can include more than one element.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless otherwise defined, all technical terms used herein have the same meaning as commonly understood by one of ordinary skill in the art to which this disclosure belongs.

Figure 1:
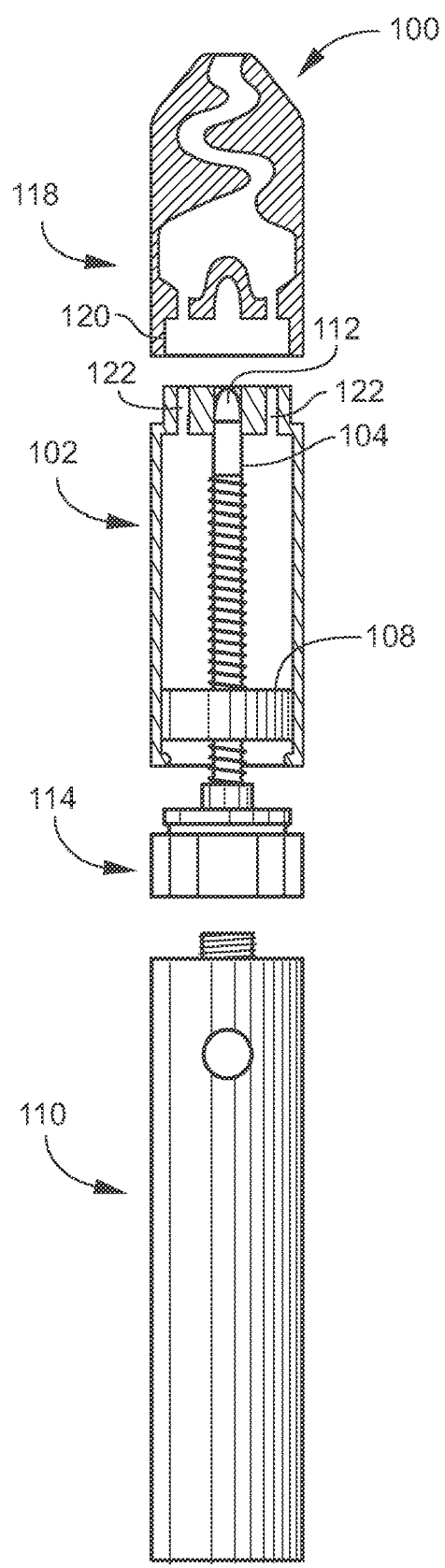
FIG. 1 is cross-sectional, side view of an example vaporizing device in accordance with embodiments of the present disclosure.

The present disclosure describes vaporizing devices that can control an amount of substance being vaporized for consumption by a user. An example, vaporizing device of the present disclosure may include a casing configured to hold a substance for vaporizing. As an example, FIG. 1 illustrates a vaporizing device 100 including a casing 102 configured to hold a substance for vaporizing. In accordance with embodiments, the substance may include an oil or other suitable liquid. For example, the substance may be a mixture of vegetable glycerin, propylene glycol, nicotine, the like, or combinations thereof. In another example, the substance may include one or more terpenes or terpenoids. In a further example, the substance may include one or more plant waxes, plant shatters, pure plant molecules, the like, or combinations thereof.

In accordance with embodiments, the casing may include one or more indicators that can measure the amount of the substance contained within the casing. In an example, the casing 102 may include a glass casing with one or more indicators etched on the glass casing. The indicator(s) can measure the amount of substance left in the casing. In another example, the casing 102 may include a window with one or more indicators positioned on the window for measuring the amount of substance within the casing. Thus, a user of the vaporizing device 100 may visually confirm the amount of substance either consumed or available to consume by observing the indicator(s) on the casing. In accordance with embodiments, the casing may be about 1⅜ inches tall and about ¾ inches in diameter, or any other suitable size. Also, in accordance with embodiments, the casing may include a metallic connector for coupling to a mechanism of the vaporizing device as described herein below. The connector may be about ⅛ inches and about ¾ inches in diameter, or any other suitable size. In accordance with embodiments, the casing may vary in size from 1 inch to about 2 inches in length, or any other suitable size.

The vaporizing device of the present disclosure may include a plunger having a heating element inserted within the casing. For example, FIG. 1 shows that the vaporizing device 100 includes a plunger assembly 104 having a heating element 106 inserted within the casing 102. In accordance with embodiments, the plunger assembly 104 can include a threaded rod. For example, FIG. 1 shows that the plunger assembly 104 includes a threaded rod 106 within casing 102. Also in accordance with embodiments, the plunger may include a stopper configured to traverse the threaded rod. Continuing the previous example, FIG. 1 also shows that the plunger assembly 104 includes a plunger stopper 108 configured to traverse the threaded rod 106. In accordance with embodiments, the plunger may be about 1¾ inches in length, or any other suitable length. It should be noted that the length of the plunger may vary in accordance with the size of the casing. For example, if the size of the casing increases by ⅛ of an inch, the plunger must also increase by about ⅛ of an inch. Also in accordance with embodiments, the stopper may be substantially ¼ inches in length and slightly less than ¾ inches in diameter to fit within the casing. It should be noted the width of the stopper may vary in accordance with the width of the casing.

In accordance with embodiments, the heating element 106 comprises a metallic heating coil configured to conduct heat within the interior of the threaded rod. For example, FIG. 3 illustrates threaded rod 106 includes a metallic heating coil 200 configured to conduct heat within the interior of threaded rod 106. In accordance with embodiments, the metallic heating coil 200 is located vertically within the center of the rod. In accordance with embodiments, the plunger is configured to couple to a battery of the vaporizing device. In embodiment embodiments, the battery may couple to the plunger via a two-wire connector. For example, FIG. 2 shows that the plunger assembly 104 is coupled to battery 110 of vaporizing device 100. In accordance with embodiments, the metallic heating coil 200 can conduct heat using energy from the battery of the vaporizing device. Continuing the previous example, the metallic heating coil 200 of FIG. 2 can conduct heat using energy from battery 110 of vaporizing device 100. In accordance with embodiments, the threaded rod may include an insulating material within the interior of the threaded rod for insulating the metallic heating coil 200. For example, threaded rod 106 of FIG. 2 may include an insulating material (not shown) within the interior of the threaded rod 106 for insulating metallic heating coil 200. In this example, the insulating material may be placed between metallic heating coil 200 and an exterior wall 202 of threaded rod 106.

The vaporizing device of the present disclosure may include a ceramic tip. In accordance with embodiments, the threaded rod may receive the ceramic tip. As an example, FIG. 1 illustrates vaporizing device 100 includes a ceramic tip 112. Continuing the previous example, FIG. 2 illustrates threaded rod 106 may receive ceramic tip 112. In accordance with embodiments, the ceramic tip comprises threading to fasten the ceramic tip to the threaded rod. For example, FIG. 3 illustrates ceramic tip 112 comprising threading 302 to fasten the ceramic tip 112 to threaded rod 106. Also, in accordance with embodiments, the ceramic tip comprises a heat sink configured to receive the metallic heating coil. Continuing the previous example, FIG. 3 illustrates ceramic tip 112 comprises a heat sink 302 configured to receive metallic heating coil 202 as shown in FIG. 2. In accordance with embodiments, the ceramic tip also comprises an element with a parabolic shape. For example, FIG. 3 illustrates ceramic tip 112 comprises an element 304 with a parabolic shape.

Figure 4A:
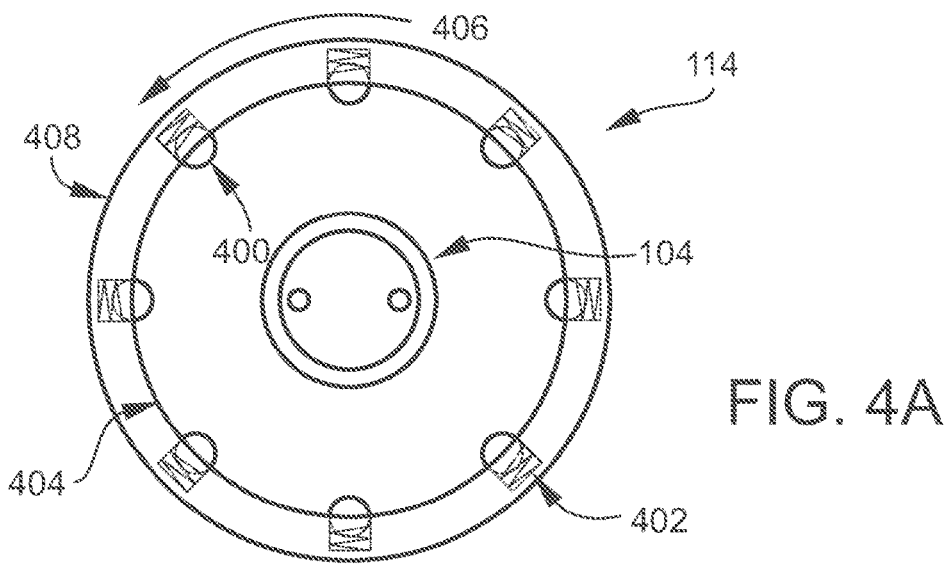
FIG. 4A is a cross-sectional, top view of an example mechanism configured to advance a material within a casing of the vaporizing device in accordance with embodiments of the present disclosure.

In accordance with embodiments, the vaporizing device of the present disclosure may include a mechanism configured to advance the substance within the casing. As an example, FIG. 1 shows the vaporizing device 100 as including a mechanism 114 configured to advance the substance within the casing. In accordance with embodiments, the mechanism 114 is configured to rotate the plunger to advance the substance in the casing. For example, FIG. 4A illustrates a cross-sectional view of a mechanism 114 configured to rotate plunger assembly 104 to advance a substance in casing 102 (not shown). In accordance with embodiments, the mechanism 114 comprises one or more ball bearings configured to rotate the plunger. Continuing the above example, FIG. 4A illustrates mechanism 114 comprises one or more ball bearings 400 configured to rotate plunger assembly 104. In accordance with embodiments, the mechanism comprises one or more grooves configured to receive the one or more ball bearings to lock the one or more ball bearings in place. Continuing the previous example, FIG. 4A illustrates mechanism 114 including grooves 402 configured to receive corresponding ball bearings 400 to lock the ball bearings 400 in place. In accordance with embodiments, the mechanism can operatively twist as the ball bearings 400 traverse a surface in between the grooves 402 in response to an applied twisting force. For example, FIG. 4A illustrates mechanism 114 operatively twists as the ball bearings 400 traverse a surface 404 in between the grooves 402 in response to an applied twisting force 406 applied at the outer surface 408 of mechanism 114.

In accordance with embodiments, the mechanism is substantially 5/16 inches tall and 3/4 inches in diameter, or any suitable size. Also in accordance with embodiments, the mechanism comprises a connector atop the mechanism for coupling to the casing. The connector is about 1/8 inches tall and 11/16 inches in diameter. Also in accordance with embodiments, the mechanism comprises a rubber seal atop the connector configured to abut the stopper. The rubber seal can be substantially 1/4 inches in diameter and 1/8 inches in length.

In an embodiment, the stopper can traverse the plunger during rotation of the plunger. Returning to FIG. 1, plunger stopper 108 can traverse the plunger assembly 104 during rotation of the plunger assembly 104. In one embodiment, the stopper can traverse the plunger to advance a substance within the casing. In another embodiment, the stopper can traverse the plunger to return the plunger to an initial position within the casing.

In accordance with embodiments, the mechanism can operatively couple to the casing and a battery of the vaporizing device. For example, FIG. 1 illustrates mechanism 114 operatively coupled to casing 102 and battery 110 of vaporizing device 100. In accordance with embodiments, the casing can include an element configured to operatively couple the casing to the mechanism. In embodiments, the element may comprise a medical grade stainless steel connection is configured to fasten to the mechanism using one of a snap-on or screw-on configuration. In accordance with embodiments, the battery may include a threaded portion configured to operatively fasten to the mechanism. For example, FIG. 1 illustrates the battery 110 with a threaded portion 116 for fastening to mechanism 114.

Figure 4B:
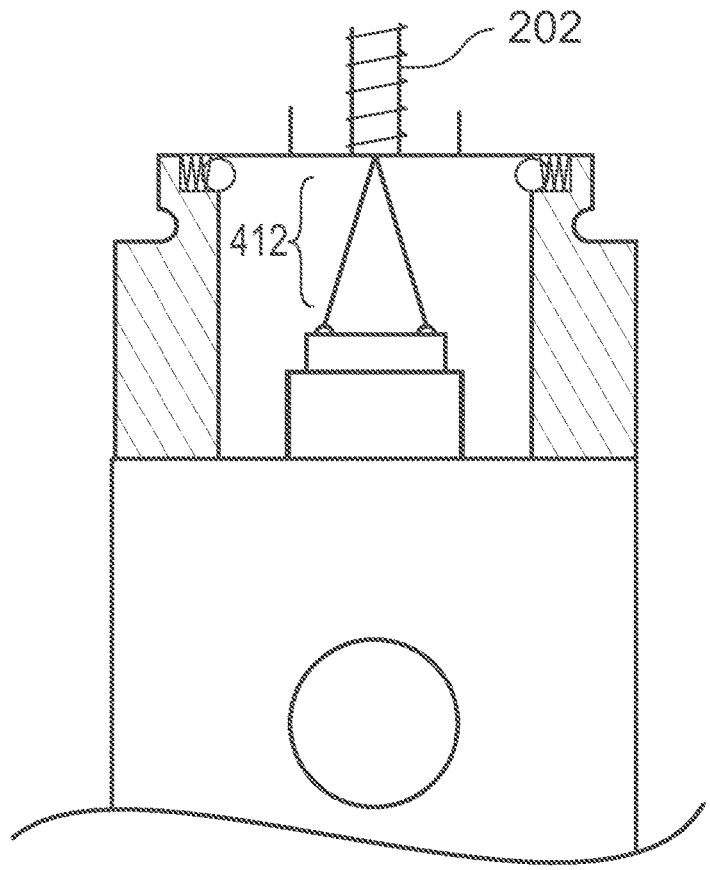
FIG. 4B is a cross-sectional, side view of the mechanism shown in FIG. 4A.

In accordance with embodiments, the mechanism is configured to connect the battery to the heating element of the plunger. For example, FIG. 4 illustrates a cross-sectional view of mechanism 114 configured to connect battery 110 to the heating element 200 (not shown in this view). In accordance with embodiments, the mechanism comprises a two-wire connector configured connect the metallic heating coil of the heating element to the battery. For example, FIG. 4 illustrates that mechanism 114 includes a two-wire connector 412 configured to connect heating element 200 to battery 110.

In accordance with embodiments, the battery is substantially 3 inches tall and 3/4 inches in diameter. Also in accordance with embodiments, the battery comprises a connector configured to couple the battery to the mechanism as described above. The connector may be about 3/16 inches tall and 1/4 inches in diameter. It should be noted that the dimensions of the connector may be set to allow standard size batteries to couple to the connector. For example, the dimensions of the connector may be set to allow a standard AA battery to couple to the connector.

Figure 5:
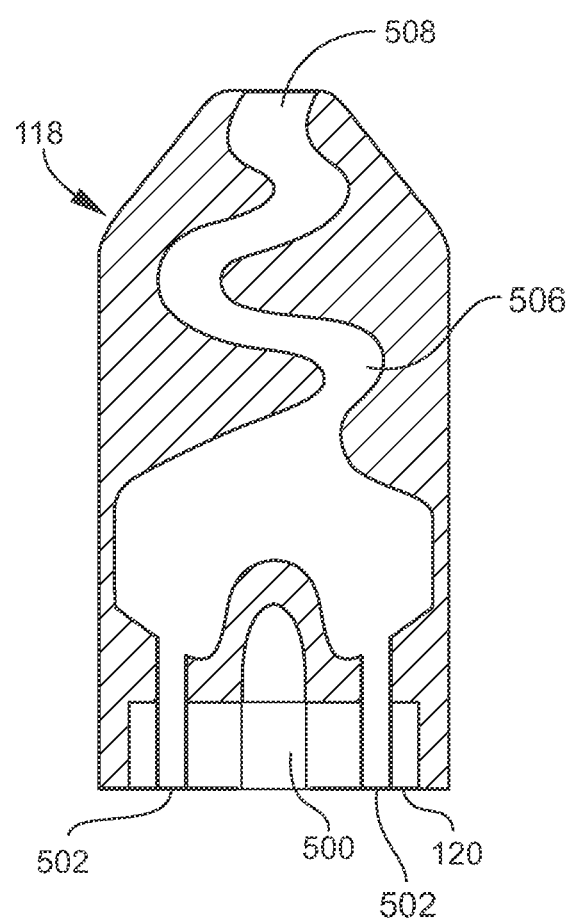
FIG. 5 is a cross-sectional, side view of a mouthpiece of the vaporizing device in accordance with embodiments of the present disclosure.

The vaporizing device of the present disclosure includes a mouthpiece comprising an atomizer configured to vaporize the substance using the heating element. Returning to FIG. 1, vaporizing device 100 comprises a mouthpiece 118 comprising an atomizer 120 configured to vaporize the substance using plunger assembly 104. In accordance with embodiments, the atomizer defines a receptacle for receiving the plunger. For example, FIG. 5 illustrates mouthpiece 118 comprising atomizer 120 defines a receptacle 500 for receiving plunger assembly 104 (not shown). In accordance with embodiments, the receptacle is defined to receive a ceramic tip of the plunger. For example, receptacle 500 of FIG. 5 is defined to receive ceramic tip 112 (not shown).

In accordance with embodiments, the mouthpiece can couple to the casing of the vaporing device. FIG. 1 illustrates, as an example, mouthpiece 118 can couple to casing 102 of vaporing device 100. In accordance with embodiments, the mouthpiece may include a connector configured to connect the mouthpiece to the casing. In one example, the connector is a metallic component configured to fasten to the casing. In one embodiment, the connector may include one or more rubber gaskets for coupling to the casing. In another embodiment, the connector may include one or more threaded sections for coupling to the casing. In accordance with embodiments, the mouthpiece may be about 1.5 inches tall and 3/4 inches in diameter at its widest point. In accordance with embodiments, the metallic component is substantially 3/16 inches tall 3/4 inches in diameter. In accordance with embodiments, the mouthpiece lengths may typically vary from about 1.5 inches tall to 2.5 inches tall. However, it should be noted the mouthpiece may be constructed to larger lengths. In accordance with embodiments, the mouthpiece may include a curved piece of glass.

In accordance with embodiments, the atomizer defines two or more channels for receiving the substance for vaporizing from the casing. Also in accordance with embodiments, the casing comprises two or more channels aligning with the two or more channels of the atomizer. For example, FIG. 5 illustrates atomizer 120 can define two or more channels 502 for receiving the substance for vaporizing from the casing 102 of FIG. 1. As shown in FIG. 1, casing 102 comprises two or more channels 122 aligning with the two or more channels of atomizer 120. In accordance with embodiments, the two or more channels of the casing rides in a connector of the casing can couple the casing to the mouthpiece. Also in accordance with embodiments, the connector of the casing is 3/16 inches tall and 11/16 inches in diameter.

The mouthpiece of the vaporizing device can also define a channel with two or more curvatures between the atomizer and an opening of the mouthpiece. For example, FIG. 5 illustrates mouthpiece 118 defines a channel 506 with two or more curvatures between the atomizer 120 and opening of the mouthpiece 508. An example advantage of a channel with two or more curvatures is the vaporized substance cools as it traverses through the curvatures of the channel to the opening of the mouthpiece.

Figure 6:
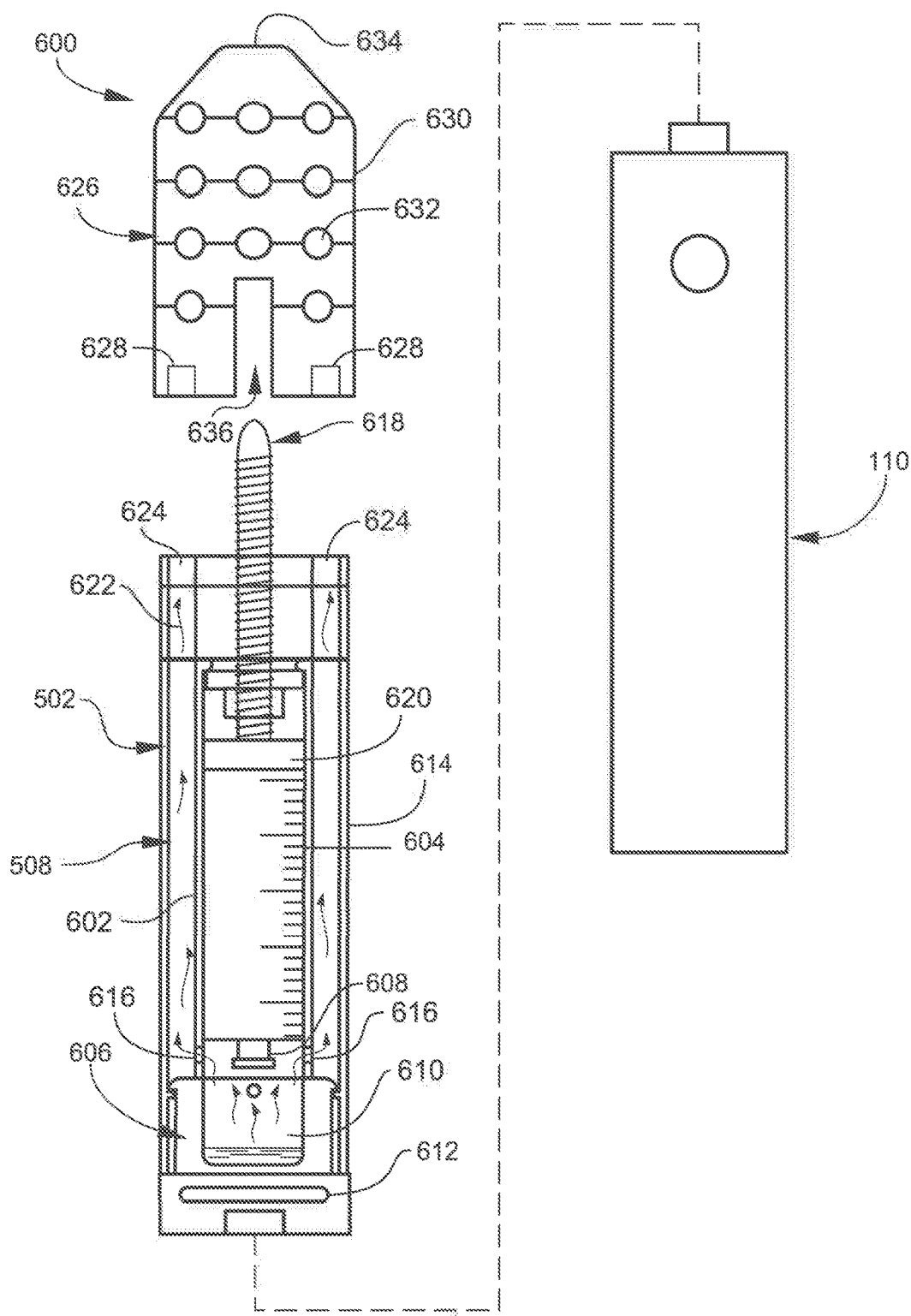
FIG. 6 is a cross-sectional, side view of another example vaporizing device in accordance with embodiments of the present disclosure.

According to another aspect, a vaporizing device of the present disclosure includes a chamber configured to hold a substance for vaporizing. For example, FIG. 6 illustrates a vaporizing device 600 including a chamber 602 configured to hold a substance for vaporizing. In accordance with embodiments, the substance comprises one of a liquid and an oil. Also in accordance with embodiments, the chamber may comprise one or more indicators measuring the amount of substance within the casing. For example, the chamber 602 may include one or more indicators 604 measuring the amount of substance in the casing. In one embodiment, the chamber may comprise a glass chamber with the one or more indicators etched on the glass casing measuring the amount of substance in the chamber. In an alternative embodiment, the chamber may comprise a window with one or more indicators on the window measuring the amount of substance within the chamber. Thus, a user of the vaporizing device could visually confirm the amount of substance either consumed or available to consume by observing the one or more indicators on the chamber. In accordance with embodiments, the chamber is substantially 1 inch tall and ¼ inches in diameter. It should be noted that the chamber size may vary in accordance with the size of the casing.

The vaporizing device may also include an atomizer configured to couple to the chamber and vaporize the substance. For example, FIG. 6 illustrates vaporizing device 600 includes an atomizer 606 configured to couple to the chamber and vaporize the substance. In accordance with embodiments, the chamber comprises a nozzle configured to deliver the substance to the atomizer. For example, FIG. 6 illustrates chamber 602 comprises a nozzle 608 configured to deliver the substance to atomizer 606, and a battery 110 (which corresponds to battery 110 as shown in FIG. 1). In accordance with embodiments, the nozzle may comprise one or more radial holes for delivering the substance to the atomizer. Also in accordance with embodiments, the vaporizing device may include a cap configured to fasten to the nozzle. Such a cap can prevent the substance from leaving the chamber when the vaporizing device is not in use. In accordance with embodiments, the atomizer is substantially 1.5 inches in diameter and $6/10^{th}$ cm tall.

In accordance with embodiments, the atomizer may include a dish configured to receive the substance from the chamber. For example, FIG. 6 shows an atomizer 606 including a dish 610 for receiving the substance from chamber 602. In accordance with embodiments, the atomizer 606 can include a heating element 612 positioned under the dish for heating the dish 610. By placing the heating element 612 under the dish 610, the heating element 612 can evenly heat the substance at a precise temperature. In accordance with embodiments, the heating element 612 can be a triple spiral flat metallic heating coil 200. In embodiments, the metallic heating coil 200 can be a platinum heating coil. During operation, the heating element 612 can operate between about 2.4 ohms and about 3.0 ohms, or another high resistance depending upon the voltage of the batter. For example, FIG. 6 shows atomizer 606 as including a heating element 612 situated under dish 610 for heating the dish 610. In accordance with embodiments, the dish is about 1 centimeters in diameter and 0.5 centimeters tall.

The vaporizing device can also include a casing configured to receive the chamber and the atomizer. For example, FIG. 6 shows a casing 614 that receives or holds chamber 602 and atomizer 606. In accordance with embodiments, the atomizer comprises two or more radial gaps for releasing the vaporized substance into the casing. As an example, FIG. 6 shows atomizer 606 comprises two or more radial gaps 616 for releasing the vaporizing substance into casing 614. In accordance with embodiments, the casing may be about 2 inches in length and about ¾ inches in diameter. It should be noted that the casing length may vary from about 1.5 to 3 inches in length. It is also noted that the casing or any other structure described herein may be any suitable size, shape, or configuration.

In accordance with embodiments, the chamber can include a threaded plunger. For example, FIG. 6 illustrates chamber 602 including a threaded plunger 618. In embodiments, the plunger 618 includes a stopper attached to a distal end of the plunger. For example, FIG. 6 illustrates plunger 618 comprises a stopper 620 attached to a distal end of the plunger 618. In accordance with embodiments, the threaded plunger is about 1 inch long, or any other suitable length. The stopper is about 1 centimeter in diameter, and $2/10$ths centimeters thick. In accordance with embodiments, the stopper can be one of a rigid rubber, a medical grade plastic, or any other suitable material. It should be noted that the stopper size may suitably vary in accordance with the dimensions of the chamber.

The vaporizing device can also include a mechanism coupled to the casing and configured to advance the substance within the chamber. For example, FIG. 6 illustrates a mechanism 622 coupled to casing 614 to advance the substance within chamber 602. In accordance with embodiments, the mechanism can receive a portion of the threaded plunger. Continuing the previous example, FIG. 6 illustrates mechanism 622 configured to receive a portion of threaded plunger 618. In accordance with embodiments, the mechanism is configured to rotate the threaded plunger to advance the material within the chamber. For example, mechanism 622 can rotate the threaded plunger 618 to advance the material within chamber 602. It should be noted that the mechanism 622 of FIG. 6 can rotate plunger 618 similarly as to mechanism 114 of FIG. 1 and FIG. 4. In accordance with embodiments, the mechanism may define two or more channels for receiving the vaporized material from the casing. For example, FIG. 6 illustrates mechanism 622 comprises channels 624 for receiving the vaporized material from casing 614. In accordance with embodiments, the mechanism is about 1 centimeter in height and about 1.5 inches in diameter.

The vaporizing device can also include a mouthpiece for receiving the vaporized material from the mechanism. For example, FIG. 6 shows a vaporizing device 600 including a mouthpiece 626 for receiving the vaporized material from mechanism 622. In accordance with embodiments, the mouthpiece can define two or more intake gaps that align with the two or more channels for receiving the vaporized material from the mechanism. For example, FIG. 6 illustrates mouthpiece 626 can have intake gaps 628 that align with the channels 624 of mechanism 622.

In accordance with embodiments, the mouthpiece can include multiple layers of radial gaps arranged between the two or more intake gaps and an opening of the mouthpiece for cooling the vaporized material. For example, FIG. 6 shows a mouthpiece 626 having multiple layers 630 of radial gaps 632. The mouthpiece 626 also has an opening 634 for cooling the vaporized material from mechanism 622. Also in accordance with embodiments, the mouthpiece can receive a portion of the threaded plunger for securing the mouthpiece to the casing. In embodiments, the mouthpiece includes a receptacle for receiving the portion of plunger.

For example, FIG. 6 shows a mouthpiece 626 that can receive a portion of threaded plunger 618 via receptacle 636 for securing mouthpiece 626 to casing 614. In accordance with embodiments, the mouthpiece is about 1 inch and 1 centimeter in height and about 1.5 inches in diameter. It should be noted that the mouthpiece length may be between about 1 inch and about 3 inches.

Figure 7:
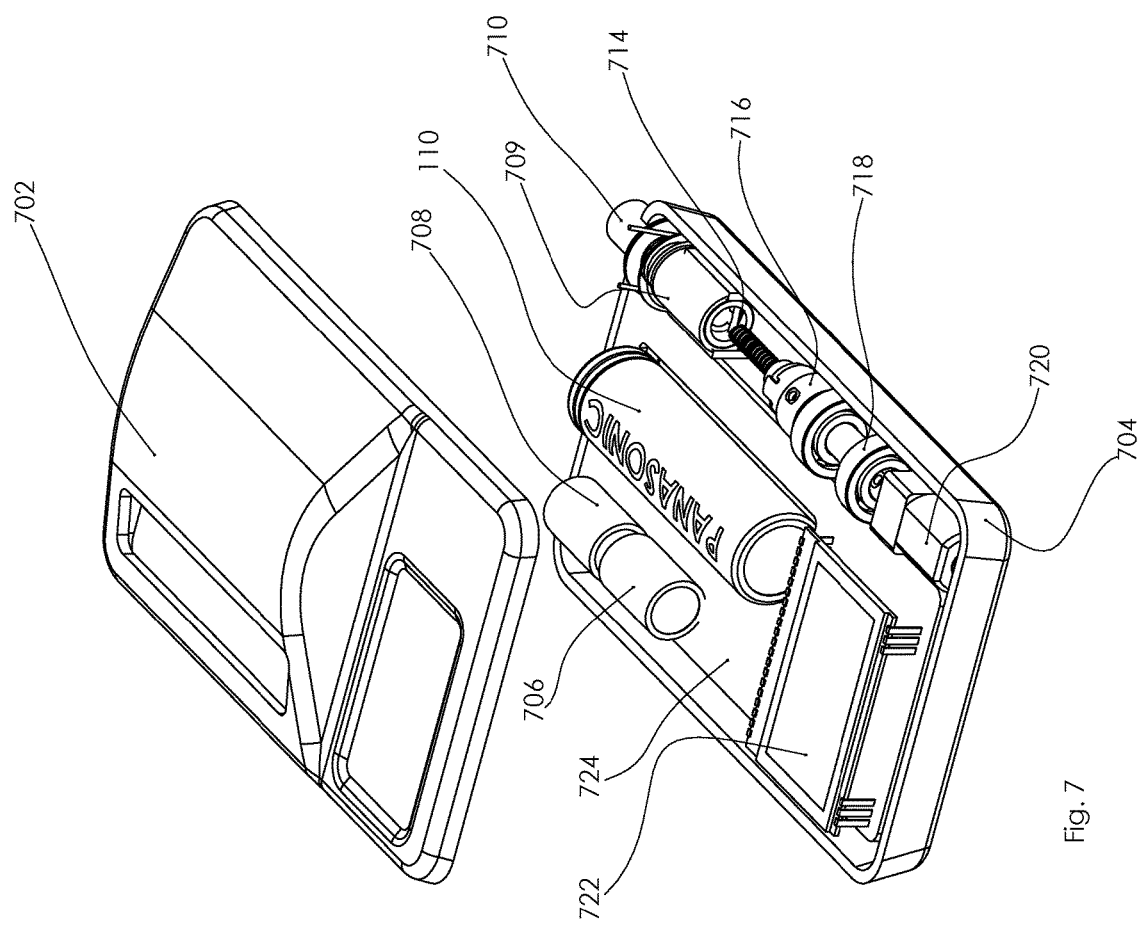
FIG. 7 is an internal view of the vaporizing device in accordance with embodiments of the present disclosure.

Now referring to FIG. 7 of the present disclosure. FIG. 7 illustrates an upper half of an outer shell casing 702 of the vaporizing device 100. As mentioned above, the outer shell casing 702 may be made of aluminum or similar material. The lower half of the outer shell casing 704 is also shown in FIG. 7. The lower half of the outer shell casing 704 may also be referred to as a lower housing. The lower half of the outer shell casing 704 can contain additional structural and electrical components of the vaporizing device 100 which will be described in detail. Attached or suitably associated to the lower half of the outer shell casing 704 is an oil cartridge 706, an oil vapor chamber 708, a vapor chamber assembly 709, battery 110 (which corresponds to battery 110 as shown in FIG. 1), vapor path mouthpiece 710, vapor path mouthpiece hole 711, linear actuators 714, 716, and 718, and 720, heating coil 715 which corresponds to heating coil 200), display 722, and an internal bottom casing 724 of the lower half of the outer shell casing 724. The internal bottom casing 724 may have space suitable enough to hold a circuit board or associated circuitry.

In accordance with these embodiments, the oil cartridge 706 may be made up of a cap, including a silicon cap which may hold oil and cap the plunger maintaining sterility and cleanliness, vapor chamber, and a cartridge. The oil cartridge may be interchangeable with a loose-leaf or dry herb cartridge which can be placed inside the vapor chamber housing. The oil cartridge 706 may contain the desired concentrate. In an alternate embodiment, the oil cartridge 706 may be a glass tube. The glass tube 706 may have a plunger in its bottom that fits over a piston. It may come with a removable silicon cap on the top to contain the concentrate within when not in use. The oil cartridge 706 may attach to the oil vapor chamber 708. Further, the oil vapor chamber 708 may attach to the oil cartridge 706. The oil may be pushed inside the oil vapor chamber 708 where it is vaporized. The chamber 708 may be made out of a thermally conductive material to ensure full vaporization. The chamber 708 may have a cap on the top which allows air to enter and exit the chamber through air ports. This allows the user to draw the vapor out of the chamber and through the cap. The cap can be removed to make the chamber easier to clean. As further shown in FIG. 7, the vapor chamber assembly 709 may be made up by both the oil cartridge 706 and the oil vapor chamber 708. It may include a silicone gasket that may seal the connection between the oil cartridge 706 and the oil vapor chamber 708. Once the two are connected they can easily be slid inside the housing of the heating element 106. The battery 110 as shown in FIG. 7 can additionally provides the highest output and safety standards according to current industry standards. The battery may be an 18650 size battery and may also be affixed to the internal bottom casing of the lower half of the outer shell casing 724. The vapor path mouthpiece 710, as shown in FIG. 7, may allow the user of the device to acquire the vapor emitted from the device. A vapor path mouthpiece aperture 711 may receive oil such that the oil can pass into the vapor chamber assembly 709. Also illustrated are linear actuators 714, 716, and 718, and 720. The linear actuators convert the motors rotation into forward and backward movement. The linear actuators may also move the piston in and out of the oil cartridge 706. The piston is attached to the lead screw using an anti-rotation collar (to be discussed in detail below). This changes the rotation into forward power for the piston to slide inside the plunger which resides in the bottom of the cartridge. As the piston moves the plunger through the cartridge, the oil is pushed into the oil vaporization chamber. As further shown, the heating coil 200 can be wrapped around rod 106 in a straight tubular manner. This design provides independent heat to the oil cartridge 706 and vapor chamber 708. It also allows a more robust and efficient heat up and cool down time for the oil cartridge 706 while also isolating the vapor chamber 708 for oils and turning both the oil cartridge 706 and vapor chamber 708 up for loose leaf. The display 722 displays a user interface which includes indicators pertaining to temperature, whether the device is on or off, various display modes, such as quick mode or advanced mode and the like. The display 722 may be any display such as, organic light emitting diode (OLED), light emitting diode (LED), liquid crystal display (LCD), plasma display panel (PDP), or the like.

Figure 8:
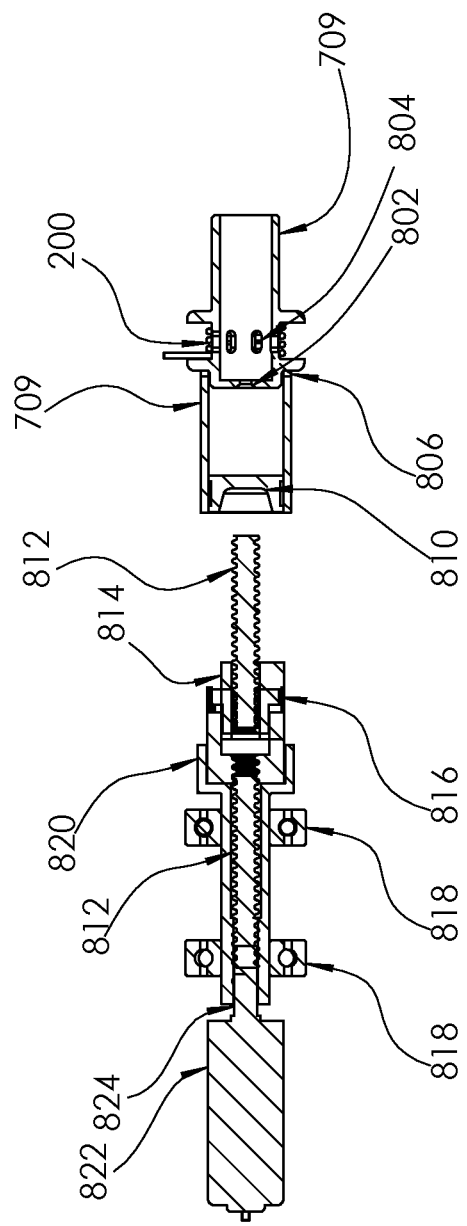
FIG. 8 is alternate design of the vaporizing device in accordance with embodiments of the present disclosure.

Now turning to FIG. 8 of the present disclosure which illustrates a perspective view of the vaporizing device according to FIG. 7. A vapor path mouthpiece hole 802 is shown to be apart of the vapor chamber assembly 709 and may allow oil to pass into the vapor chamber assembly 709. The vapor chamber assembly 709 further includes a vapor chamber air path 804 which leads into the vapor chamber assembly 709. The heating coil 200 is also illustrated in FIG. 8 being attached within the vapor chamber assembly 709. The heating coil 200 may also correspond to or be interchangeable with a heating foil. Also, a connection component 806 is attached between the oil cartridge 706 and the oil vapor chamber 708.

As further shown in FIG. 8, the "plunger cap" 810 may be attached inside 806 of the oil cartridge 706. The linear actuator 714, 716, 718, and 720 may include an outer screw 812, a lead screw guide turn stop 814 which may function to drive the outer screw 812, a lead screw guide inner housing 816 which may be attached to the inner housing to stop rotation of the drive, and outer screw bearings 818. The linear actuator 714, 716, 718, and 720 may further include an outer housing 820. The outer screw 812 may be attached to a motor 822. The motor 822 illustrated in FIG. 8 may correspond to a pololu motor 822. The motor 822 is connected to the motor shaft 824. The motor shaft 824 may also be a pololu motor shaft.

Figure 9:
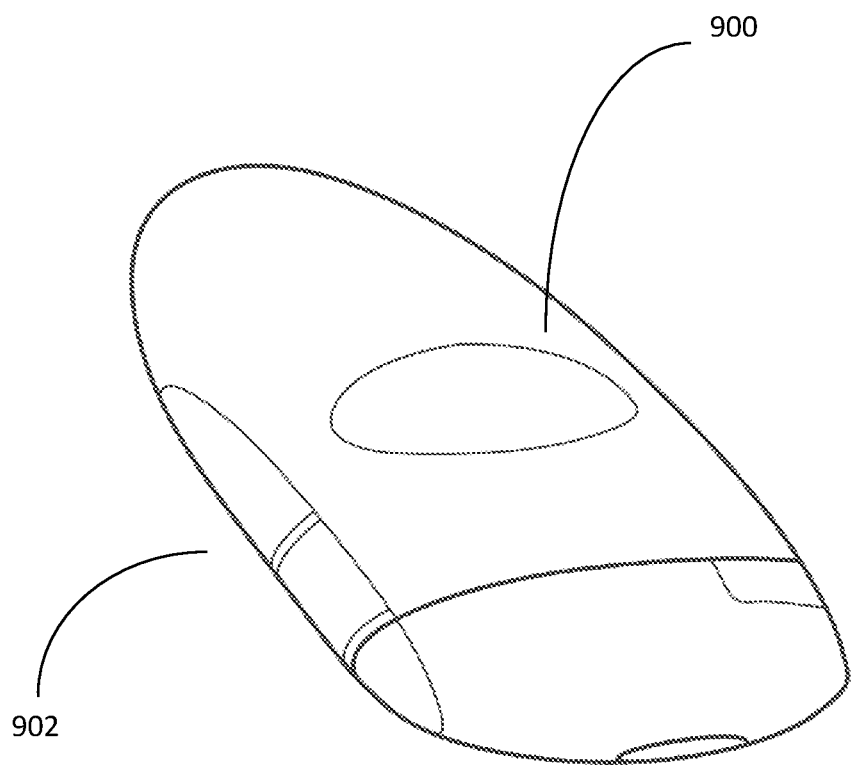
FIG. 9 is perspective top view of the vaporizing device in accordance with embodiments of the present disclosure.
Figure 10:
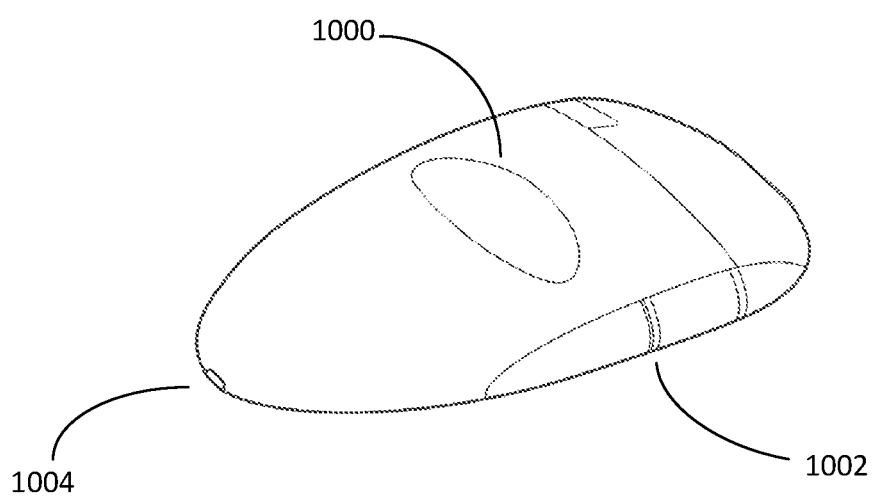
FIG. 10 is perspective top view of the vaporizing device in accordance with embodiments of the present disclosure.

FIG. 9 is alternate design illustrating a perspective view of the vaporizing device in accordance with embodiments of the present disclosure. Side buttons 902 are located on each side of the vaporizing device. The side buttons 902 are used to activate and deactivate the vaporizing device. The side buttons 902 may also be used to toggle between various settings programmed within the device. Also shown is the display 900 which is located at the center of the vaporizing device. FIG. 10 also illustrates a side perspective view of the right (or left) side of the vaporizing device. Side buttons 1002 can function to activate and deactivate the vaporizing device. Both the side buttons 902 and 1002 may be pressed simultaneously with the side buttons 902 in order to activate, deactivate, or toggle between options presented on the device. A mouthpiece 1004 is shown which may be configured to receive the vaporized material from the mechanism. Also shown is the display 1000 which is located at the center of the vaporizing device.

The embodiments of the vaporizing device as disclosed above can be incorporated into a variety of uses. For instance, users of the vaporizing device may operate the device in a Quick Mode setting or an Advanced Mode setting. For instance, in a Quick Mode setting, the user may activate the vaporizing device by pushing both side buttons 902 located on the sides of the device 3 times in a repetitious manner. The same can be done in order to deactivate the device. It is noted that when the device is deactivated, the lead screw 814 may automatically retract. Once the device is activated, a welcome screen may appear on the display 722 and displays which type of cartridge is within the device, e.g. loose leaf or oil. Once this occurs, the device can display two options for the user to select from: (1) Quick Mode; or (2) Advanced Mode. The user may be able to toggle between devices by pushing the buttons located closest to the display of the option. For instance, if the display shows Quick Mode on the left side of the screen, then the button corresponding to the left side of the screen should be selected. As such, if the display shows Advanced Mode on the right side of the screen, then the button corresponding to the right side of the screen should be selected.

In Quick mode, if selected, and the oil cartridge is installed, the device will use the preset temperature and dosage size that is preset within the device. The device may also be preset using the advanced mode operation of the application. Once the device reaches the preset temperature, it may instruct the user to push one of the side buttons of the device to initiate the motor 822 which will allow the user to use the device via vapor path mouthpiece 710. When the user utilizes the oil cartridge, the user may push the button again for the same size dosage. The device will remain heated for up to 15 seconds after each iteration in which the motor is engage. The device includes an automatic shut-off inactive status feature where the device may automatically shut-off after 15 seconds if the motor is not engaged via pressing the side button to activate the motor. The user may change the automatic shut-off inactive status feature of the motor to extend up to 30 seconds.

In Quick mode, if selected, and the loose-leaf cartridge is installed, the device will use the preset temperature and dose size that is preset within the device. The device may also be preset using the advanced mode operation of the application. Once the device reaches the preset temperature, the display may show "ready" and the device will remain heated for 5 minutes. The device's automatic shut-off inactive status feature will not execute until after 5 minutes of inactivity by the motor or if the motor is not engaged via pressing the side button to activate the motor. However, the user may extend the session for 10 minutes by pressing the side buttons of the device.

If the user selects Advance Mode, and an oil cartridge is installed, the device will first request the dosage size of the substance. Using the dial located on the device, the user may select from half dose, whole dosage, 1.5 times dose, and 2 times a dose. The dosage metrics may also include 0.5, 1.0, 1.5, 2.0. Once the desired dosage is selected, the temperature dial will display the selected temperature. The user may toggle through the various temperature settings and further select a desired setting using the side buttons. The side buttons on the device may be used to scroll and push both side buttons at the same time in order to make a selection.

Once selected, the device can activate once more, begin the heating process and display an indication that the device is ready for use. As a side note, users may use the associated application downloaded on a remote mobile computing device, such as an IPHONE®, to adjust the settings of the vaporizing device 100. For instance, the user may activate their application and select advance settings in order to calculate dosage amounts using the percentage of active ingredient of the tested product substance. The application may provide the user with an estimation of how much of a percentage of substance is actually in each dosage size selected.

If the user selects Advance Mode, and loose-leaf cartridge is installed, the device will first request the dosage size of the substance. Using the dial located on the device, the user may select from half dose, whole dosage, 1.5 times dose, and 2 times a dose. The dosage metrics may also include 0.5, 1.0, 1.5, 2.0. Once the desired dosage is selected, the temperature dial will display the selected temperature. The user may toggle through the various temperature settings and further select a desired setting using the side buttons. The side buttons on the device may be used to scroll and push both side buttons at the same time in order to make a selection. Once selected, the device will activate once more, begin the heating process and display an indication that the device is ready for use.

Figure 11:
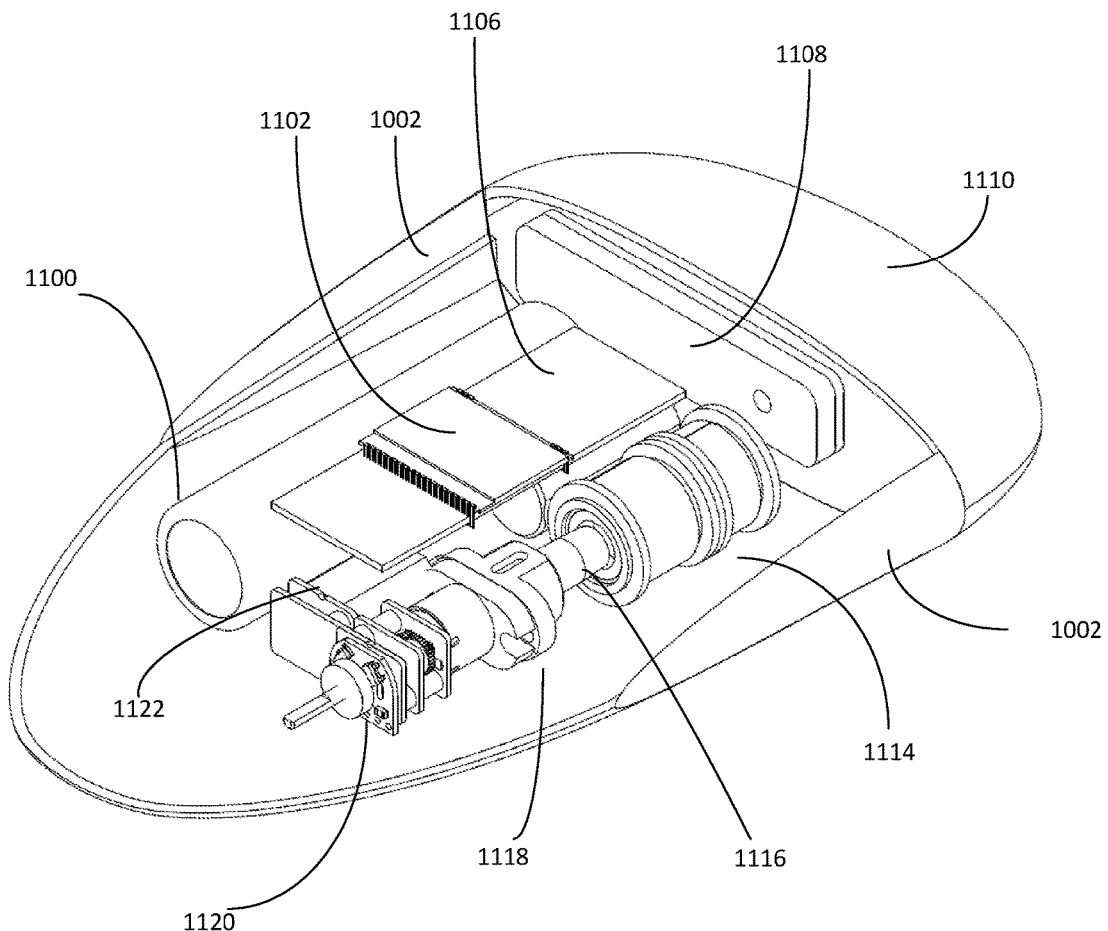
FIG. 11 is perspective top view of an alternate internal design of the vaporizing device in accordance with embodiments of the present disclosure.

FIG. 11 is perspective top view of an alternate internal design of the vaporizing device in accordance with embodiments of the present disclosure. FIG. 11 includes battery 1100 which can be affixed to the lower housing of the device and can include a rechargeable 18650 ion battery. The display 1102 and circuit board 1106 may be positioned adjacent from each other. The circuit board 1106 may be any type of circuit board known in the art including a protected or printed circuit board. Side buttons 1002 are further illustrated as appearing on the sides of the device. Ceramic cooling plates 1108 are shown behind the attached circuit board 1106. The ceramic cooling plates 1106 may include an inner path and contain two-parts which may be separated apart. A mouthpiece cooling chamber 1110 is further illustrated at the back of the device boarding the side buttons 1002. The housing 1114 that the heating element 612 is wrapped around can be filled with either loose leaf or oil within the oil vapor chamber 708. The plunger 1116 which is explained in greater detail above, is further illustrated in the alternate design of FIG. 11. The plunger 1116 is attached to an anti-rotation collar assembly 1118, which in turns is attached to an encoder 1120. The anti-rotation collar assembly 1118 may also attach to the lead screw 814. The encoder 1120 controls the speed and position of the motor 1122. The encoder 1120 may also be known as an encoder motor 1120.

Figure 12:
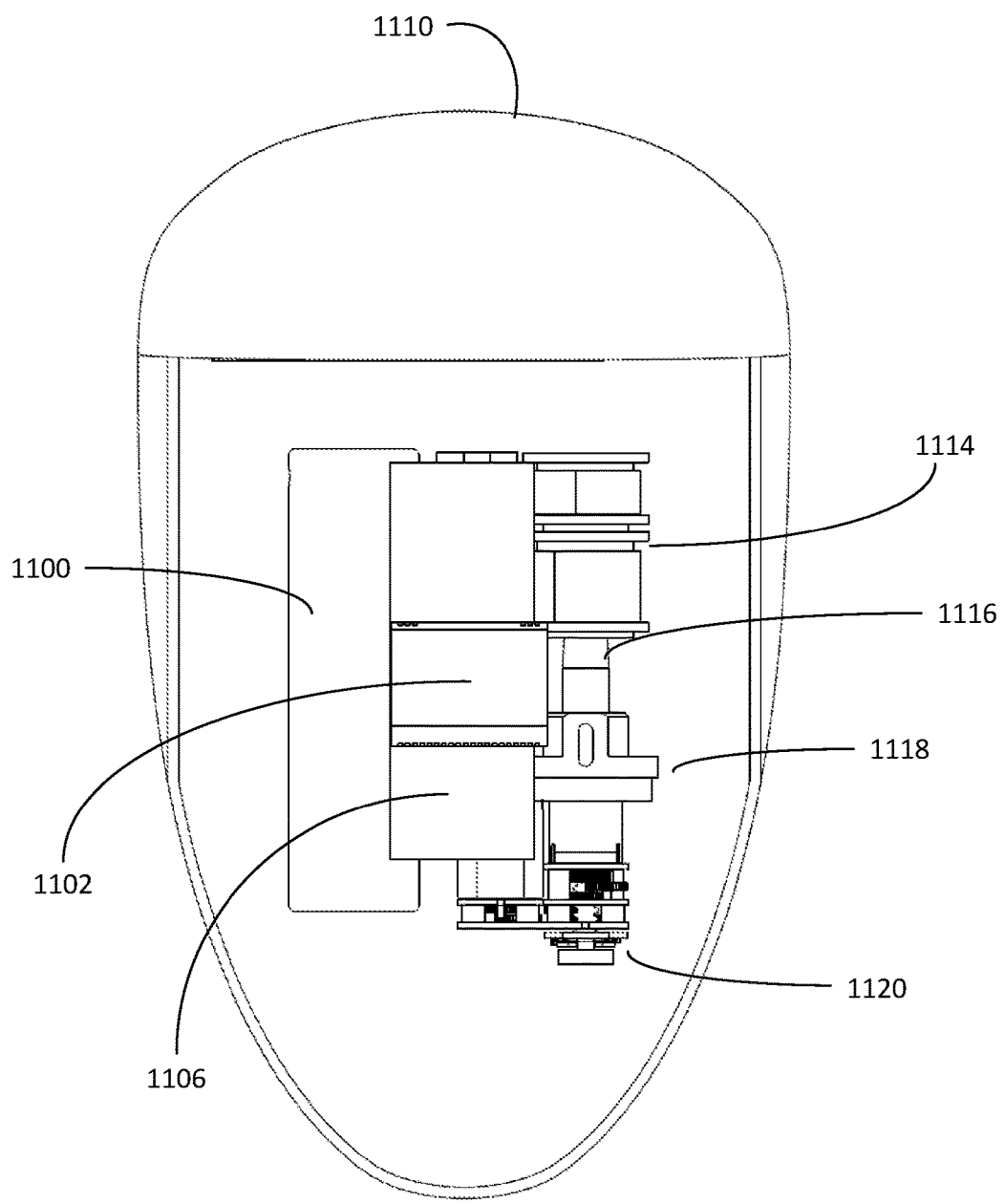
FIG. 12 is bottom view the alternate internal design of FIG. 11 in accordance with embodiments of the present disclosure.
Figure 13:
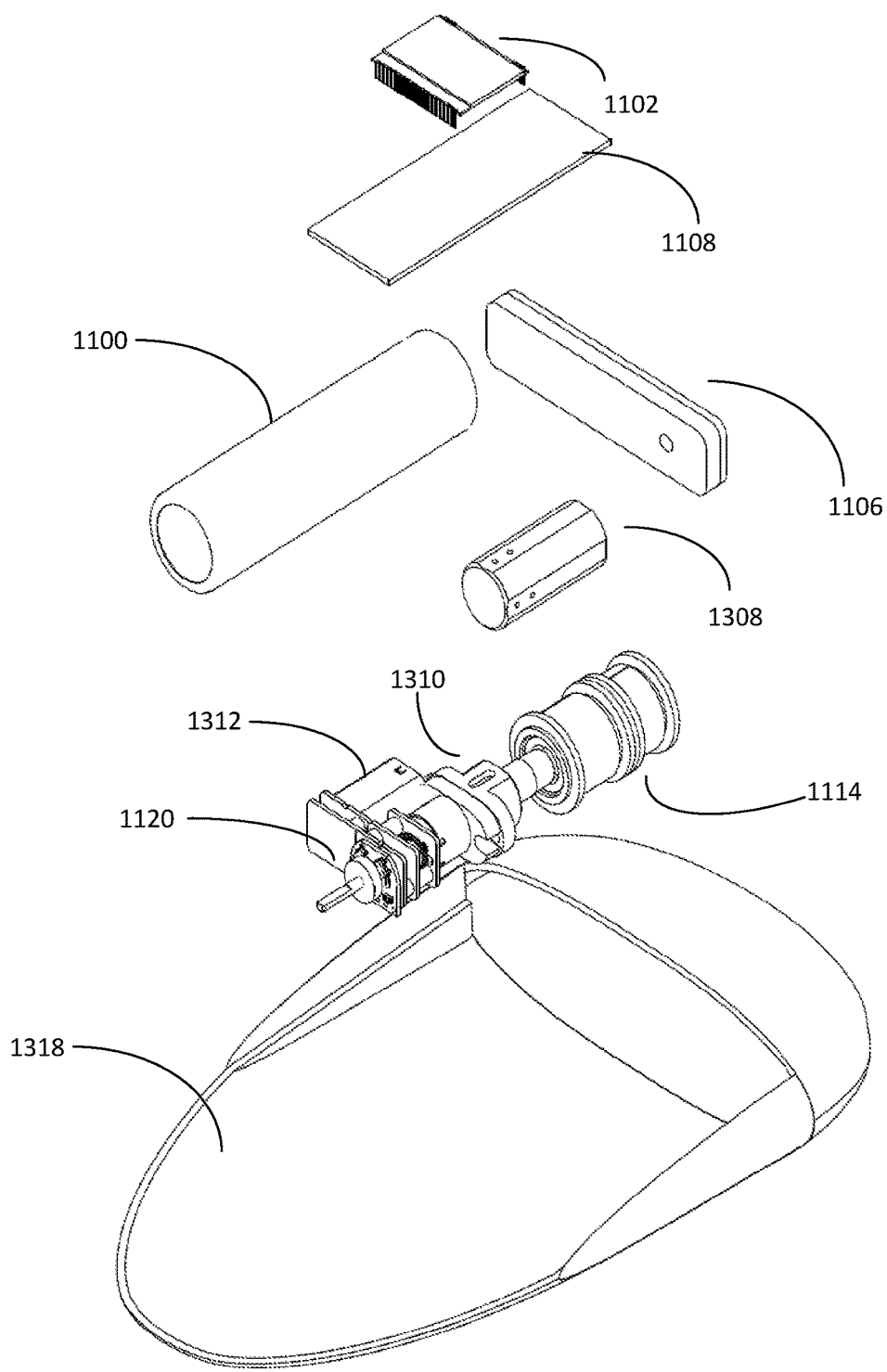
FIG. 13 is a perspective top exploded view of the internal design of FIG. 11 in accordance with embodiments of the present disclosure.
Figure 14:
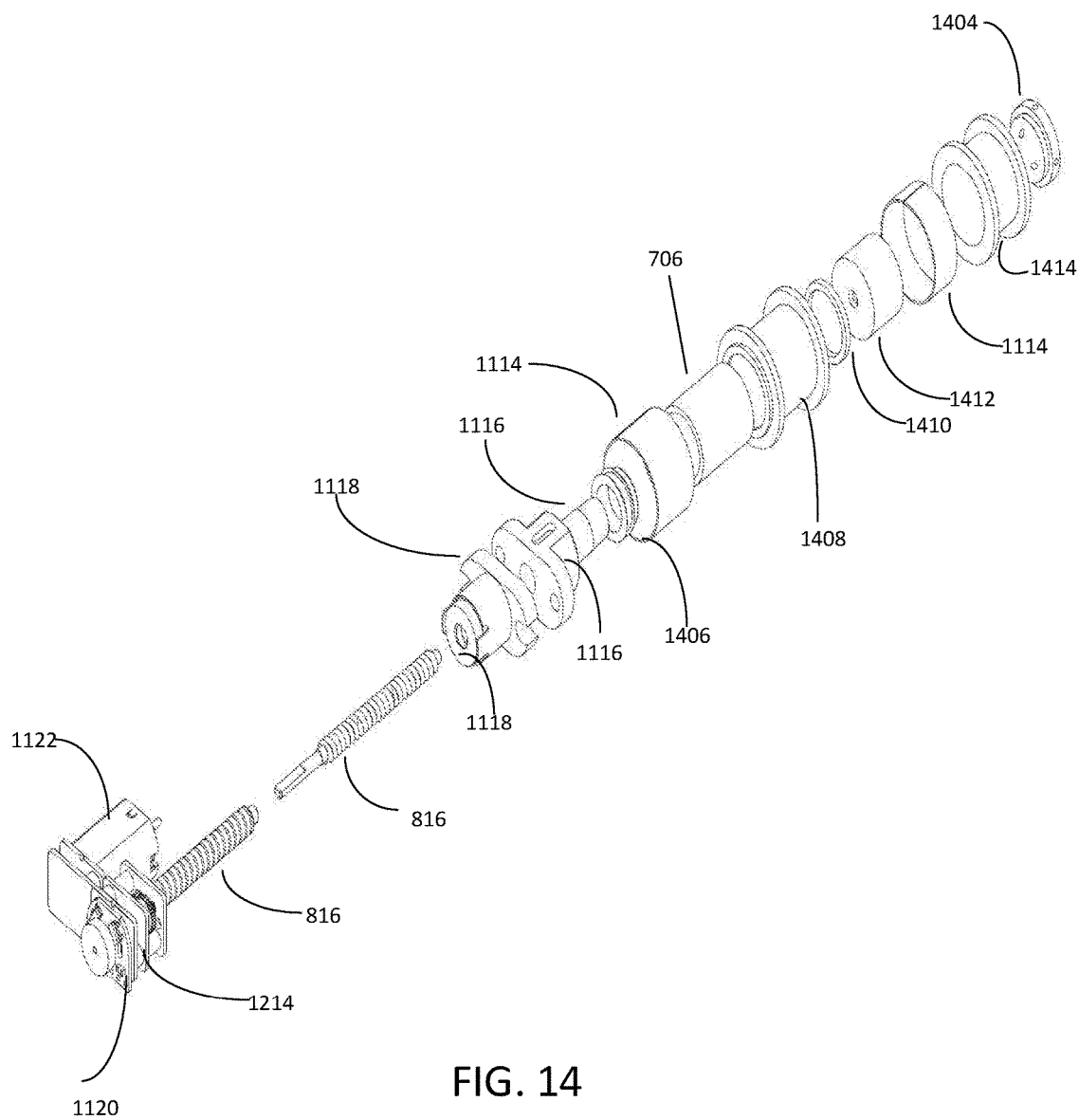
FIG. 14 is perspective exploded top view of an alternate design of the vaporizer in a device in accordance with embodiments of the present disclosure.

FIG. 12 illustrates a bottom view of the alternate internal design of FIG. 11. In addition, FIG. 12 illustrates a gear box 1214 and encoder rod 1216. FIG. 13 is a perspective top exploded view of the internal components of FIG. 11 in accordance with embodiments of the present disclosure. In addition, a loose-leaf vapor chamber 1308, anti-rotation collar plunger assembly 1310, lower housing 1318, motor 1312 (which may correspond to the motor 822 and the motor 1122), and the encoder 1120 which controls the speed and position of the motor 1312 (which may correspond to motor 822 and motor 1122) are illustrated. The loose-leaf vapor chamber 1308 may be interchanged with the oil vapor chamber 708. The anti-rotation collar plunger assembly 1310 connects the plunger 1116 to lead screw 816. The anti-rotation collar plunger assembly 1310 may also prevent the plunger 1116 and lead screw 816 from turning so as to inhibit the functionality of the vaporizer. The anti-rotation collar plunger assembly 1310 may also connect to the anti-rotation collar assembly 1118. FIG. 14 is perspective exploded top view of the structural components of the vaporizer as shown in FIG. 11 in accordance with embodiments of the present disclosure. The perspective exploded top view for FIG. 14 includes all the components disclosed in FIG. 11, as well as additional components from FIG. 11.

For instance, FIG. 14 discloses the anti-rotation collar assembly 1118. The anti-rotation collar 1118 may convert its rotation into forward or backward force. FIG. 14 further discloses a cap 1404, an oil cartridge housing 1408, and a gasket interface 1410. The gasket interface 1410 seals the Oil Cartridge connection to the oil chamber. This may prevent oil from being pushed into the gap when the piston is pushing the plunger and also force the oil to take the path of least resistance into the oil vaporization chamber. FIG. 14 also discloses a vapor chamber housing 1414 and an oil heating chamber 1412. The oil heating chamber is made of a thermally conductive material and is heated up by the heaters 106. The chamber is heated to the vaporization temperature of the oil. Converting it into a gas which is then inhaled by the user. The cap 1404 may hold oil and also cap or close the plunger, thus, maintaining sterility and cleanliness. The cap 1404 may also be attached to the oil cartridge 704. The dry herb or loose-leaf cartridge may be placed inside the vapor chamber housing 1414 instead of the oil vapor chamber housing. One cartridge (e.g. loose-leaf or oil) may be stored in one chamber, such as the oil heating chamber, vapor chamber, or loose-leaf chamber, and the other cartridge may be placed inside of the oil heating chamber housing.

While certain embodiments have been described, these embodiments have been presented by way of example only, and are not intended to limit the scope of the presently disclosed subject matter. Indeed, the novel methods, devices, and systems described herein may be embodied in a variety of other forms. Furthermore, various omissions, substitutions, and changes in the form of the methods, devices, and systems described herein may be made without departing from the spirit of the inventions. The accompanying claims and their equivalents are intended to cover such forms or modifications as would fall within the scope and spirit of the presently disclosed subject matter.

What is claimed:

1. A vaporizing device comprising:
   a chamber that holds a substance for vaporizing;
   an atomizer that couples to the chamber and vaporizes the substance;
   a dish that receives the substance from the chamber;
   a casing that receives the chamber and the dish;
   a mechanism coupled to the casing, wherein the mechanism advances the substance within the chamber; and
   a mouthpiece that receives the vaporized substance from the mechanism.

2. The vaporizing device of claim 1, wherein the substance comprises one of a liquid and an oil.

3. The vaporizing device of claim 1, wherein the chamber comprises a nozzle that delivers the substance to the atomizer.

4. The vaporizing device of claim 1, wherein the atomizer comprises:
   a heating element situated under the dish that heats the dish.

5. The vaporizing device of claim 4, wherein the atomizer comprises two or more radial gaps for releasing the vaporized substance into the casing.

6. The vaporizing device of claim 1, wherein the chamber comprises a threaded plunger.

7. The vaporizing device of claim 6, wherein the mechanism:
   receives a portion of the threaded plunger; and
   rotates the threaded plunger to advance the substance within the chamber.

8. The vaporizing device of claim 7, wherein the mechanism further defines two or more channels that receive the vaporized substance from the casing.

9. The vaporizing device of claim 8, wherein the mouthpiece comprises two or more intake gaps that align with the two or more channels for receiving the vaporized substance from the mechanism and multiple layers of radial gaps arranged between the two or more intake gaps and an opening of the mouthpiece for cooling the vaporized substance.

10. The vaporizing device of claim 6, wherein the mouthpiece receives a portion of the threaded plunger to secure the mouthpiece to the casing.

* * * * *